(12) United States Patent
Holman et al.

(10) Patent No.: US 7,842,056 B2
(45) Date of Patent: Nov. 30, 2010

(54) CUTTING MEMBER FOR BIFURCATION CATHETER ASSEMBLY

(75) Inventors: Thomas J. Holman, Minneapolis, MN (US); Jan Weber, Maastricht (NL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 555 days.

(21) Appl. No.: 11/750,748

(22) Filed: May 18, 2007

(65) Prior Publication Data

US 2008/0288041 A1    Nov. 20, 2008

(51) Int. Cl.
*A61B 17/22*    (2006.01)
(52) U.S. Cl. .................... 606/159; 606/194
(58) Field of Classification Search .......... 606/108, 606/159, 170, 191, 192, 194; 604/22, 95.03, 604/96.01, 101.01, 103.05, 103.07, 103.08, 604/508, 509; 623/1.11, 1.35
See application file for complete search history.

(56) References Cited

U.S. PATENT DOCUMENTS

| | | | |
|---|---|---|---|
| 6,146,356 A | 11/2000 | Wang et al. | |
| 6,210,429 B1 | 4/2001 | Vardi et al. | |
| 6,325,826 B1 | 12/2001 | Vardi et al. | |
| 6,692,483 B2 | 2/2004 | Vardi et al. | |
| 6,706,062 B2 | 3/2004 | Vardi et al. | |
| 7,008,438 B2 * | 3/2006 | O'Brien | 606/159 |
| 2003/0040770 A1 | 2/2003 | Radisch, Jr. | |
| 2004/0138737 A1 | 7/2004 | Davidson et al. | |
| 2004/0162516 A1* | 8/2004 | Mandrusov et al. | 604/21 |
| 2004/0176837 A1 | 9/2004 | Atladottir et al. | |
| 2005/0060027 A1* | 3/2005 | Khenansho et al. | 623/1.35 |
| 2005/0119678 A1* | 6/2005 | O'Brien et al. | 606/159 |
| 2005/0137616 A1* | 6/2005 | Vigil | 606/170 |
| 2006/0178685 A1 | 8/2006 | Melsheimer | |
| 2006/0184191 A1 | 8/2006 | O'Brien | |
| 2007/0060863 A1 | 3/2007 | Goeken et al. | |

FOREIGN PATENT DOCUMENTS

| WO | 20070075986 | 7/2007 |
|---|---|---|
| WO | 20080016406 | 2/2008 |

OTHER PUBLICATIONS

U.S. Appl. No. 60/776,149, filed Feb. 22, 2006 by Malewicz et al.

* cited by examiner

*Primary Examiner*—Todd E Manahan
*Assistant Examiner*—Katherine M Dowe
(74) *Attorney, Agent, or Firm*—Crompton, Seager & Tufte, LLC

(57) ABSTRACT

A catheter assembly for deployment in a vessel includes a catheter shaft extending from a proximal end portion to a distal end portion. A balloon is operatively coupled to the distal end portion of the catheter shaft. At least one cutting member is coupled to the catheter assembly. As the balloon is inflated, the cutting member is moved to a position to cut a portion of the vessel.

4 Claims, 7 Drawing Sheets

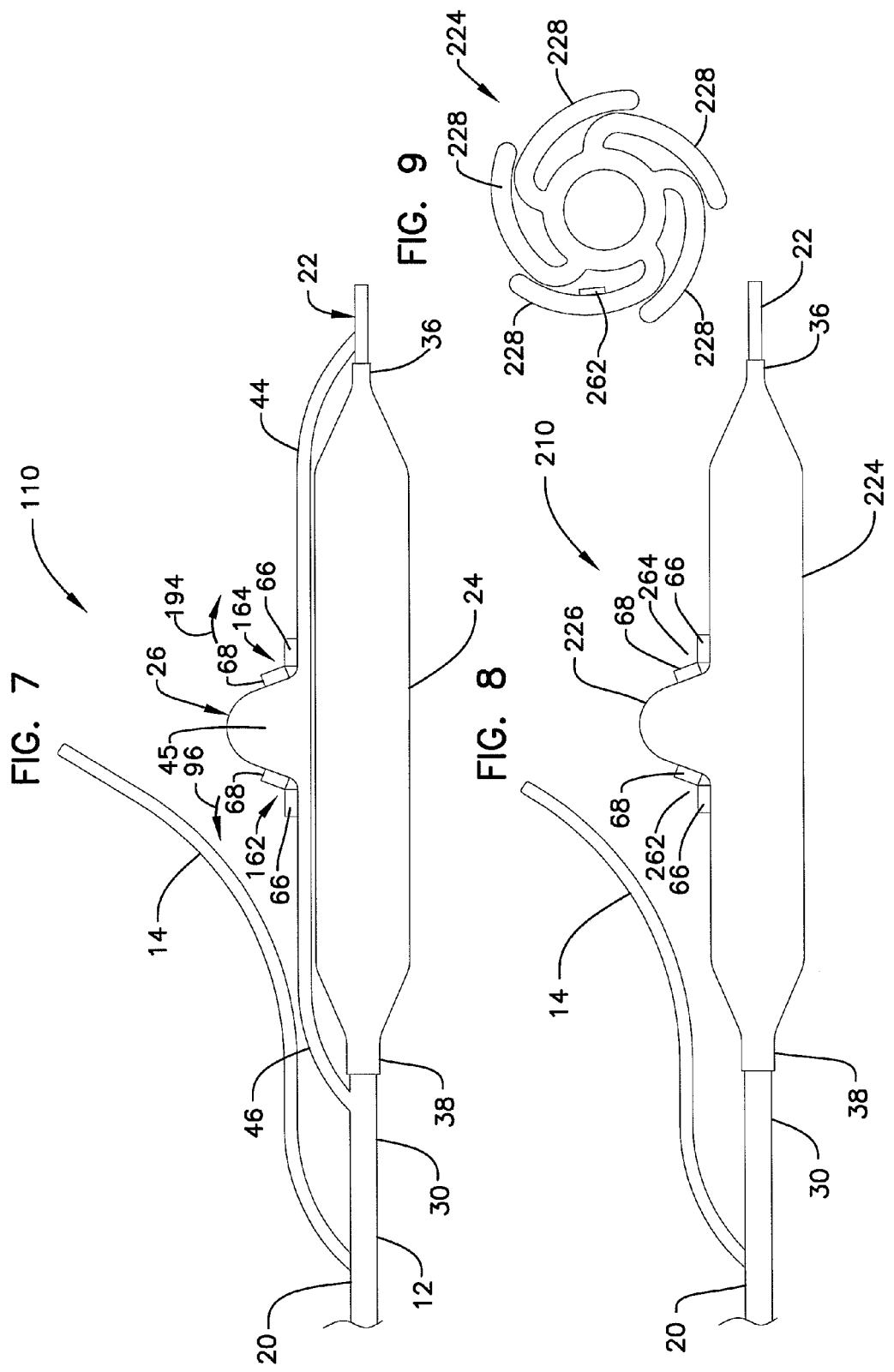

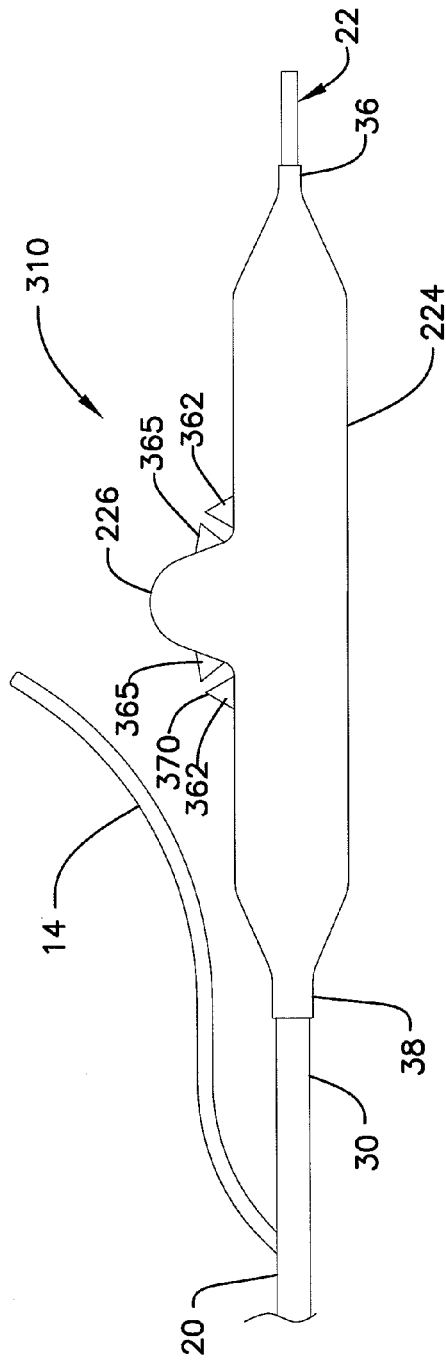
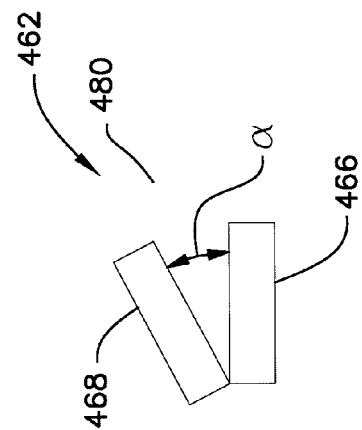
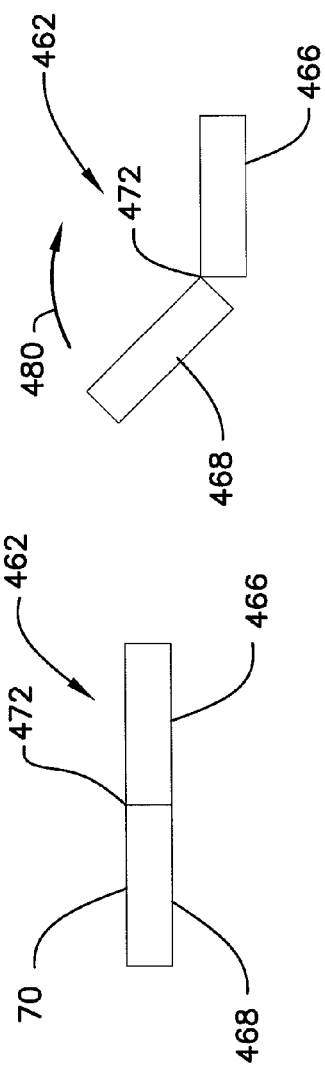

CUTTING MEMBER FOR BIFURCATION CATHETER ASSEMBLY

TECHNICAL FIELD

This disclosure relates to catheter systems and methods for treating vessel bifurcations.

BACKGROUND

Catheters are used with stents and balloon inflatable structures to treat strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular body organ for treating conditions such as, for example, occlusions, stenoses, aneurysms, dissection, or weakened, diseased, or abnormally dilated vessel or vessel wall, by expanding the vessel or by reinforcing the vessel wall. Once delivered, the stents can be expanded using one or more inflation members such as balloons. Stents can improve angioplasty results by preventing elastic recoil and by remodeling of the vessel wall and treating dissections in blood vessel walls caused by balloon angioplasty of coronary arteries. Stents can also be used as a drug delivery medium for treatment of damaged portions of a vessel.

While conventional stent technology is relatively well developed, stent technologies related to treatment of the region of a vessel bifurcation are still being developed. One challenge related to treatment of a vessel bifurcation involves the minimization of restenosis of the treated vessel.

SUMMARY

The present disclosure relates generally to catheter assemblies for treatment of bifurcated lumens in a patient, such as vessel bifurcations.

In one arrangement, a catheter assembly for deployment in a vessel includes a catheter shaft extending from a proximal end portion to a distal end portion. A balloon is operatively coupled to the distal end portion of the catheter shaft. At least one cutting member is coupled to the catheter assembly. As the balloon is inflated, the cutting member is moved to a position to cut a portion of the vessel.

There is no requirement that an arrangement or method include all features characterized herein to obtain some advantage according to this disclosure.

DESCRIPTION OF THE DRAWINGS

FIG. 7 is a schematic representation of a distal portion of another example catheter assembly for treatment of a vessel bifurcation shown in a deployed state.

FIG. 8 is a schematic representation of a distal portion of another example catheter assembly for treatment of a vessel bifurcation shown in a deployed state.

FIG. 9 is a schematic end view of the balloon of the distal portion of the catheter assembly of FIG. 8 in a non-deployed state.

FIG. 10 is a schematic representation of a distal portion of another example catheter assembly for treatment of a vessel bifurcation shown in a deployed state.

FIG. 11 is a schematic view of an example cutting member.

FIG. 12 is another schematic view of the cutting member of FIG. 11.

FIG. 13 is another schematic view of the cutting member of FIG. 11.

DETAILED DESCRIPTION

I. Overview

This disclosure relates to bifurcation treatment systems, catheter assemblies, and related methods of treating bifurcations in a patient's body. The term "bifurcation" means a division location from one unit into two or more units. Generally, two types of bifurcations of a body organ include: 1) a main tubular member defining a main lumen and a branch tubular member defining a branch lumen that extends or branches off from the main tubular member, wherein the main and branch lumens are in fluid communication with each other; and 2) a primary or main member defining a primary or main lumen (also referred to as a parent lumen) that splits into first and second branch members defining first and second branch lumens. The term "lumen" means the cavity or bore of a tubular structure such as a tubular organ (e.g., a blood vessel).

Example applications of the principles disclosed herein include cardiac, coronary, renal, peripheral vascular, gastrointestinal, pulmonary, urinary, and neurovascular systems. Bifurcated vessels in such systems can become partially or fully blocked over time, which is referred to as stenosis of the artery. There are various procedures to treat the stenosis of a vessel, including angioplasty and/or the placement of a stent at the point of stenosis to reopen the vessel. Restenosis of the bifurcated vessel can occur over time. It is desirable to minimize the effects of restenosis.

The catheter assemblies, systems and methods disclosed herein can be used for locating a branch vessel of the vessel bifurcation and for treatment of stenoses of such vessels. In some examples, the catheter assemblies include one or more cutting members that are used to cut the vessel tissue at or near the stenosis. As used herein, the term "cut" means to gash, incise, slash, slit, open, or otherwise penetrate. In one example, the cutting is done during delivery of a therapy, such as the placement of a stent relative to the vessel bifurcation for treatment of the vessel bifurcation. Other arrangements are possible. In the examples shown, the cutting of the vessel tissue can help to minimize restenosis of the vessel.

II. The Example Illustrated in FIGS. 1-6

An example catheter assembly 10 is shown schematically with reference to FIGS. 1-6. The catheter assembly 10 is configured for treatment of a vessel bifurcation, such as a vessel bifurcation 80 described below.

Figure 1:
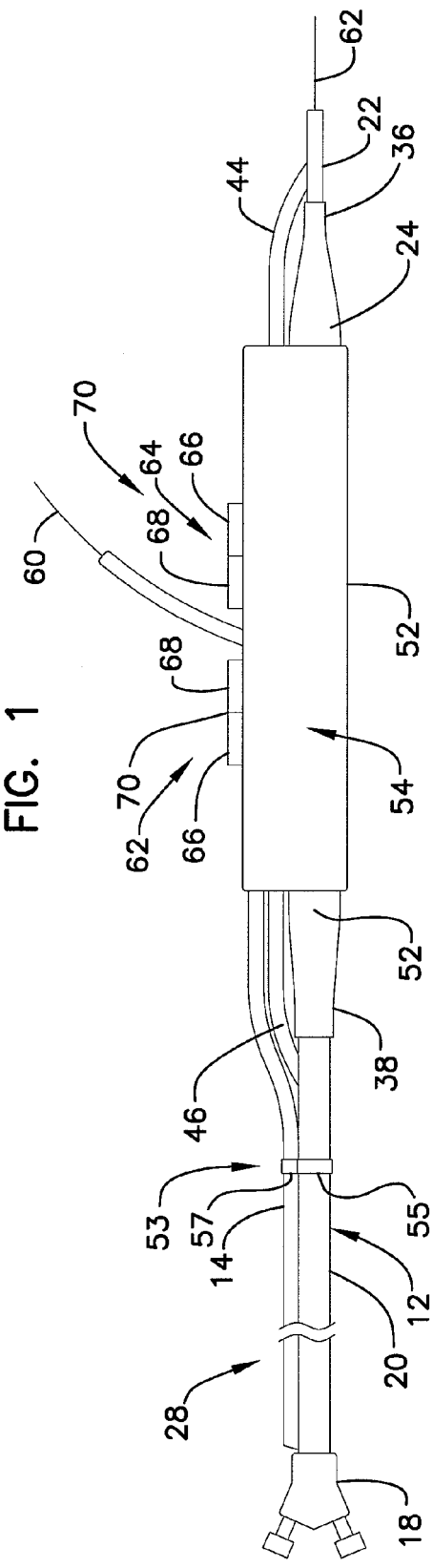
FIG. 1 is a schematic representation of an example catheter assembly for treatment of a vessel bifurcation shown in a non-deployed state.

Referring now to FIG. 1, the catheter assembly 10 includes a main catheter branch 12 and a side catheter branch 14. The main catheter branch 12 includes a catheter shaft 20 having a proximal end portion 28 with a proximal end 18 and a distal end portion 30. The catheter shaft 20 defines a main inflation lumen extending therethrough. The main catheter branch 12 further includes a main guidewire housing 22. The main guidewire housing 22 defines a main guidewire lumen.

The main catheter branch 12 further includes a main balloon 24 extending along the guidewire housing 22. A proximal waist 38 of the main balloon 24 is operably mounted to the catheter shaft 20, and a distal waist 36 of the main balloon 24 is operably mounted to the main guidewire housing 22.

The main catheter branch 12 further includes a side balloon 26. See FIG. 3. The side balloon 26 includes an inflatable portion 45, a distal waist 44, and proximal waist 46. The side balloon 26 generally extends around the main balloon 24.

The waist members 44, 46 define a side inflation lumen through which inflation fluid is provided to the side balloon 26. When uninflated, the inflatable portion 45 of the side balloon 26 maintains a generally collapsed profile. When inflated as shown in FIG. 3, the inflatable portion 45 of the side balloon 26 extends radially outward relative to the longitudinal axis of the main balloon 24.

Typically, the distal waist 44 is operably mounted to the main guidewire member 22 distal of the main balloon 24, and the distal waist 44 is also operably mounted in fluid communication with the side balloon 26. The proximal waist 46 is operably mounted in fluid communication to the inflation portion 45. The proximal waist 44 is also operably mounted to the distal end portion of the catheter shaft 20 in fluid communication with the main inflation lumen therein. The main balloon 24 is also coupled in fluid communication with the inflation lumen.

Figure 3:
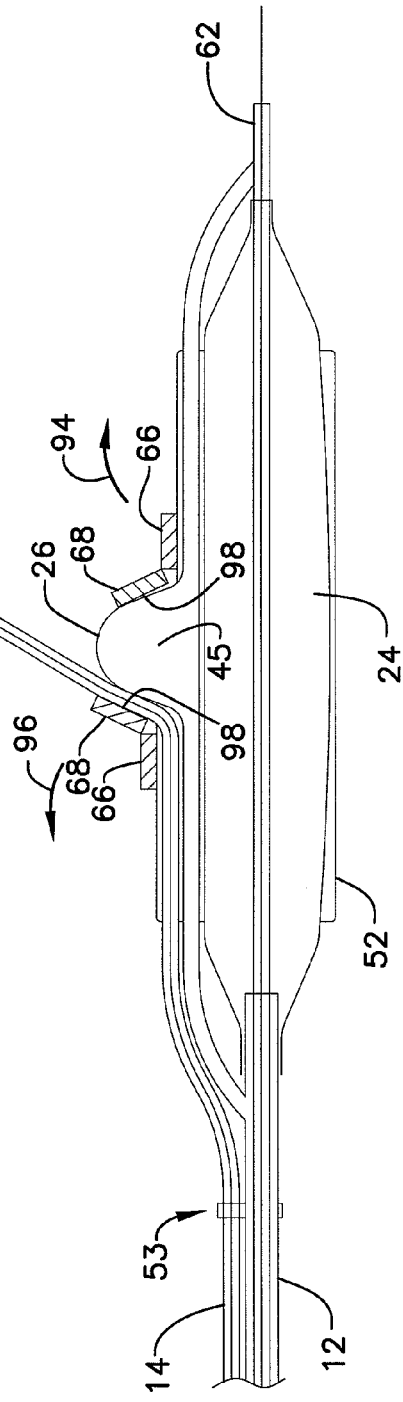
FIG. 3 is a schematic cross-sectional view of the distal portion of the catheter assembly of FIG. 1 shown in a deployed state.

As shown in FIGS. 1 and 3, the side catheter branch 14 extends generally along the catheter shaft 20. In examples, the side catheter branch 14 is generally parallel to the catheter shaft 20, although other configurations are possible. The side catheter branch 14 has a side guidewire lumen extending therethrough. The side catheter branch 14 is used to align features of the catheter assembly 10 with the ostium into the branch vessel, as described below.

In the example shown in FIGS. 1 and 3, the side catheter branch 14 is coupled to the main catheter branch 12 by a ring assembly 53. The ring assembly 53 including a first portion 55 coupled to the main catheter branch 12 so that the ring assembly 53 is fixed axially with respect to the main catheter branch 12. In the example shown, the ring assembly 53 is positioned proximally on the main catheter branch 12 approximately one inch from the proximal waist 38 of the main balloon 24. Other positions are possible. A second portion 57 of the ring assembly 53 is coupled to the first component 55 such that the second portion 57 can rotate about the first component 55. The side catheter branch 14 is coupled to the second portion 57 so that the side catheter branch 14 can rotate about the main catheter branch 12, while being fixed axially by the ring assembly 53.

Figure 2:
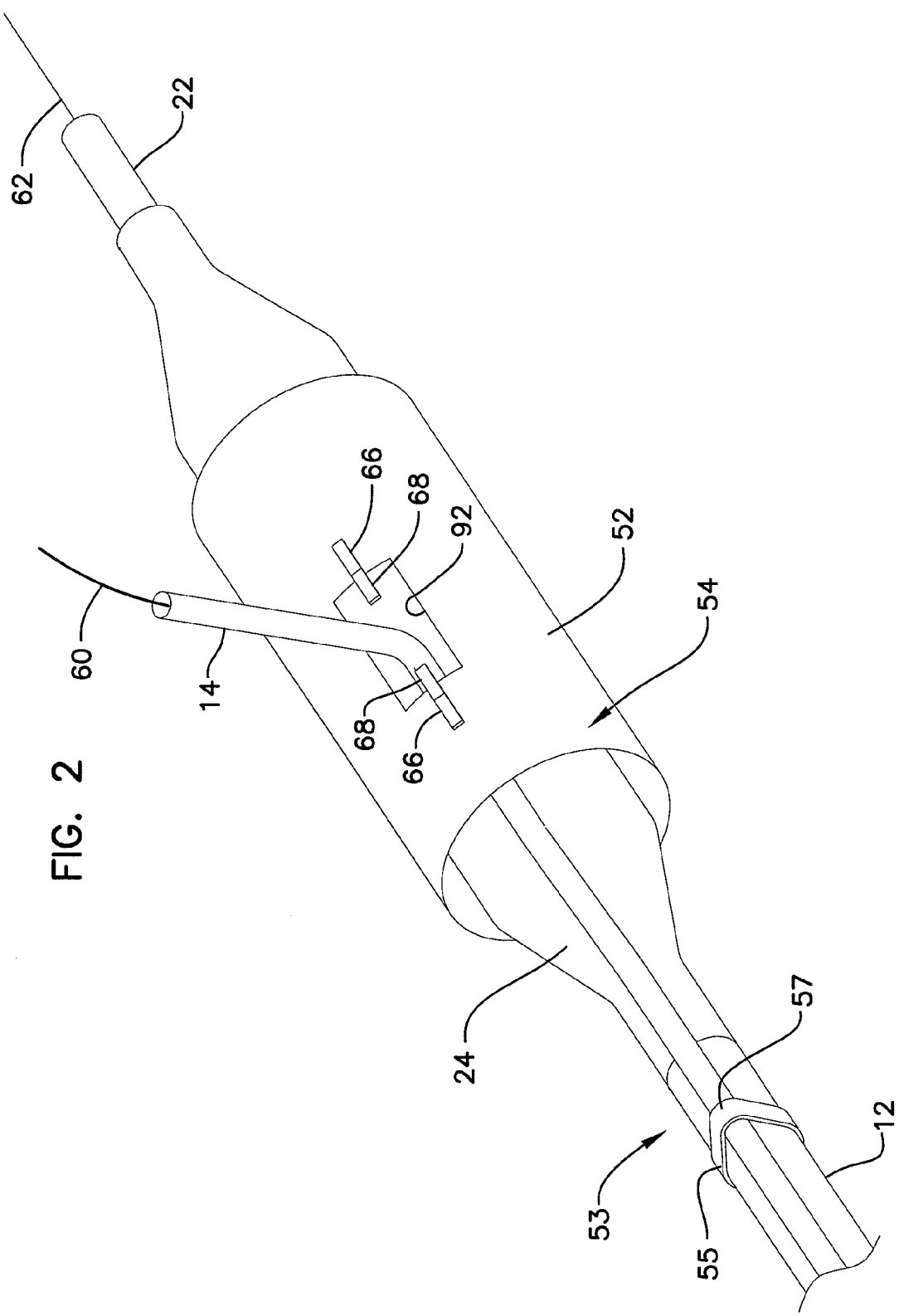
FIG. 2 is a schematic perspective representation of a distal portion of the catheter assembly of FIG. 1.

Referring to FIGS. 1-3, positioned about the main and side balloons 24, 26 is a sheath 52. In example arrangements, the sheath 52 is crimped or otherwise attached to the balloons 24, 26 and/or the side catheter branch 14. For example, in one arrangement, the sheath 52 is coupled to the side catheter branch 14 so that the sheath 52 can rotate about the main catheter branch 12 to a desired orientation.

Attached to an outer circumference 54 of the sheath 52 are one or more articulated cutting members, such as cutting members 62, 64. Each cutting member 62, 64 includes a first cutting portion 66 and a second cutting portion 68. In the example shown, the first cutting portions 66 of each of the cutting members 62, 64 are coupled to the outer circumference 54 of the sheath 52.

The second cutting portions 68 are rotatably coupled to the first cutting portions 66 so that the second cutting portions 68 can pivot with respect to the first cutting portions 66. In example arrangements, the second cutting portions 68 can pivot generally outwardly away from the outer circumference 54 of the sheath 52. For example, the second cutting portions 68 can rotate generally radially outwardly from the outer circumference 54. In some arrangements, the second cutting portions 68 rotate in a direction generally perpendicular to a longitudinal axis of the main catheter branch 12. In one arrangement, the second cutting portions 68 are positioned to extend adjacent to and overlap an aperture 92 formed in the sheath 54 (see FIG. 2), such that the side balloon 26 can extend through the aperture 92 to contact and pivot the second cutting portions 68.

For example, referring now to FIG. 3, the catheter assembly 10 is shown with the main and side balloons 24, 26 in expanded form in the deployed state. As the side balloon 26 is expanded, the inflatable portion 45 extends through the aperture 92 in the sheath 52 (see FIG. 2) to engage a lower surface 98 of the second cutting portions 68 of the cutting members 62, 64. As the inflatable portion 45 expands, the inflatable portion 45 forces the second cutting portions 68 to pivot in opposite directions 94, 96 with respect to the first cutting portions 66. In this manner, the first and second cutting portions 66, 68 can be forced against and cut the stenosis in the main and branch portions of the vessel, as described further below.

An outer surface 70 of each cutting member 62, 64 is configured to cut tissue, such as a stenosis in the bifurcated vessel. For example, in one embodiment, the outer surface 70 includes a sharpened edge that can be used to mechanical cut the stenosis. In other arrangements, the outer surface 70 can be used to deliver other therapies that are capable of cutting the stenosis, such as Radio Frequency (RF), ultrasonic, or other electromechanical ablation therapies.

The cutting members 62, 64 can be delivered to the stenosis in the bifurcated vessel using a variety of methods. For example, as described below with reference to FIGS. 4-6, the outer surface 70 of the cutting members 62, 64 can be coated with a material, such as polymeric material, that covers the cutting members 62, 64 so that the cutting members 62, 64 do not cut the blood vessel during delivery of the cutting member 62, 64 to the stenosis. Once at the desired site, the polymeric material can be removed so that the outer surface 70 can be used to cut the stenosis. For example, in one arrangement, the coating is removed by applying an electrical charge to the cutting members 62, 64 to erode the polymeric material. In other embodiments, the cutting members 62, 64 are configured such that, as the cutting members 62, 64 are employed as described below, the outer surface 70 cuts through the coating to cut the blood vessel.

In yet other arrangements, the cutting members 62, 64 can be folded against the outer circumference 54 of the sheath 52 during delivery. When the cutting members 62, 64 reach the stenosis, the cutting members 62, 64 can be mechanically moved into the cutting position. In one example, the cutting members 62, 64 are moved into the cutting position using hydraulic pressure from the fluid in the inflation lumens for the main and side balloons 24, 26. In another embodiment, electricity is used to excite a ferrofluidic fluid within the balloons 24, 26 and/or a lumen connected to the cutting members 62, 64 to cause the cutting members 62, 64 to move from a stowed position to the cutting position, or the cutting members 62, 64 can themselves include Electroactive Polymers (EAP). In another arrangement, the cutting members 62, 64 can be made of a shape member material such as nitinol. In yet another example, an outer sheath can be placed over the cutting members 62, 64 during delivery. The outer sheath can be removed once the cutting members 62, 64 are at the stenosis to allow the cutting members 62, 64 to cut the stenosis.

In yet another example, the cutting members 62, 64 can be coupled directly to the main or side balloons. See FIGS. 7 and 8. In such arrangements, the cutting members can be encompassed within the folds of the main or side balloons during delivery. See FIG. 9. Upon expansion of the main or side balloons, the cutting members 62, 64 are exposed to allow the cutting members 62, 64 to cut the walls of the vessels. Other examples are possible.

In yet other examples, a plurality of cutting members can be mounted about the circumference of the sheath 52. Upon delivery the sheath 52 extends at least partially into the bifurcated vessel, so that the cutting members located on the sheath can cut the bifurcated vessel. The cutting members on the sheath can also contact portions of the main vessel to cut any stenosis located in the main vessel as well. Other configurations are possible.

Figure 4:
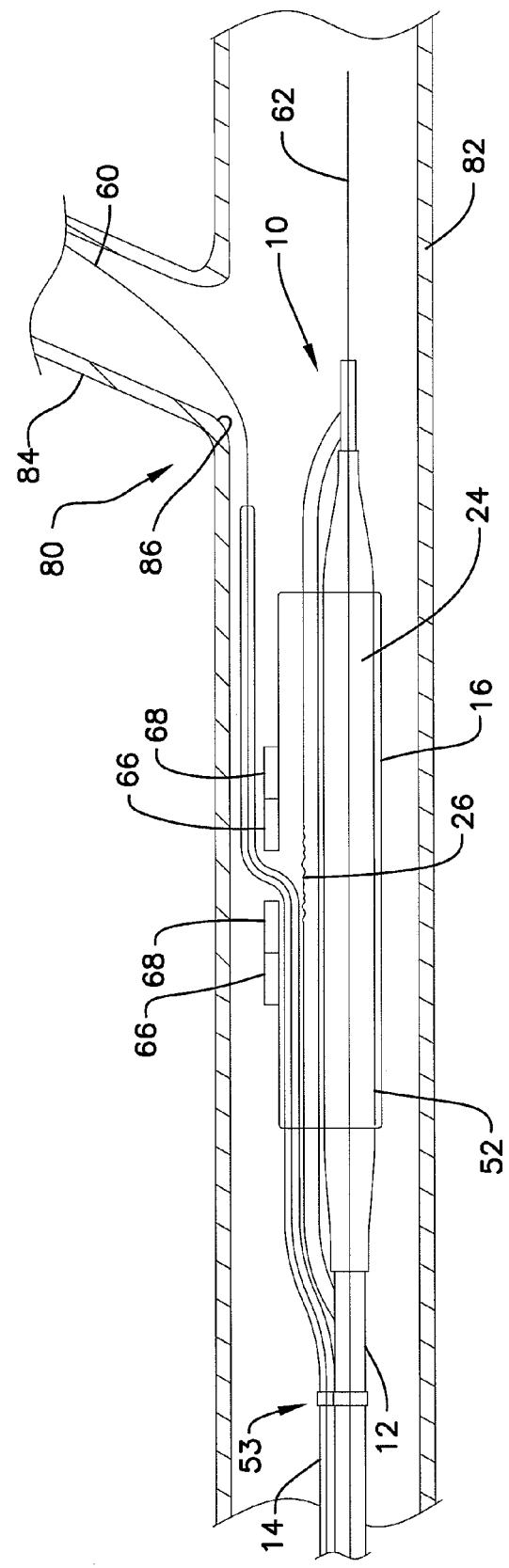
FIG. 4 is a schematic side view of the catheter assembly shown in FIG. 1 in a position prepared for treatment of a vessel bifurcation.
Figure 5:
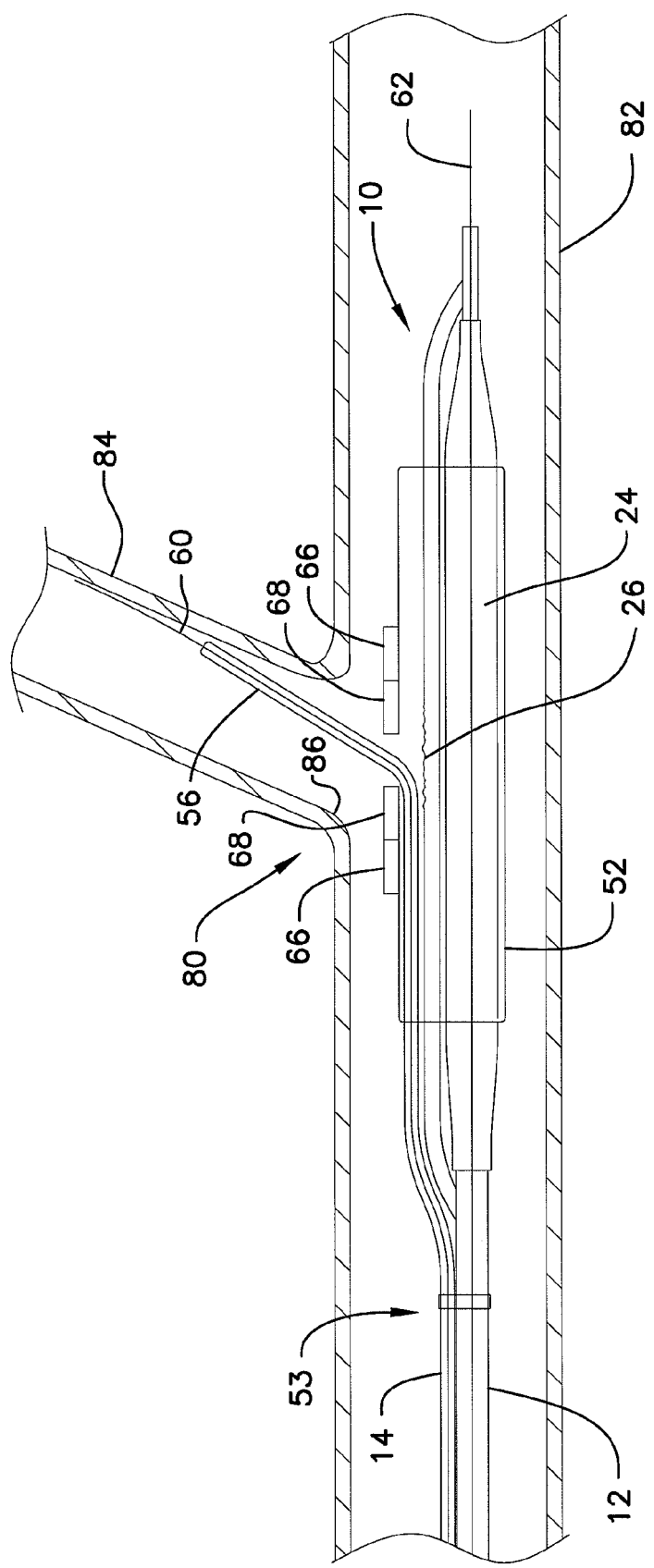
FIG. 5 is a schematic side view of the catheter assembly shown in FIG. 4 with the side catheter branch extending into a branch vessel of the vessel bifurcation.
Figure 6:
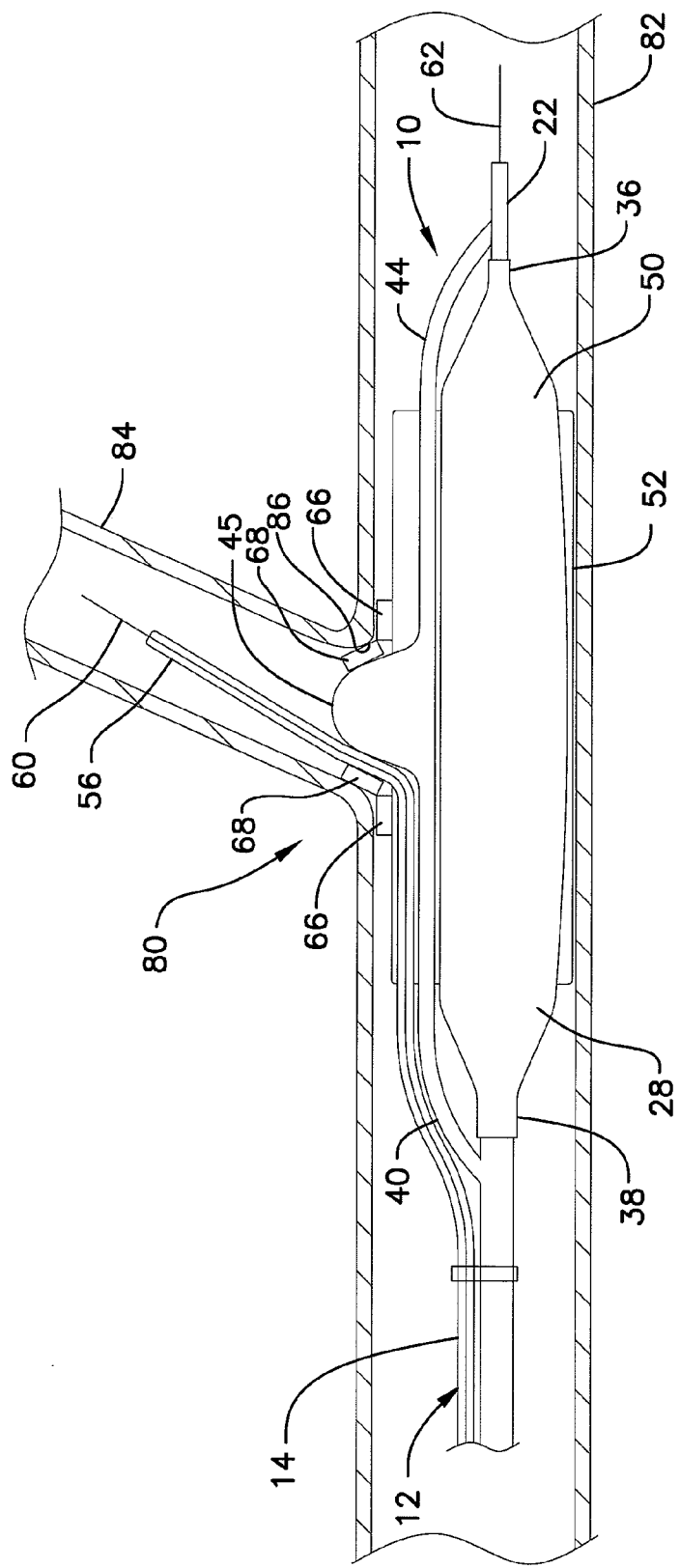
FIG. 6 is a schematic side view of the catheter assembly shown in FIG. 5 with the side and main balloons inflated at the vessel bifurcation.

Referring now to FIGS. 4-6, the catheter assembly 10 can be used for treatment of the vessel bifurcation 80. Typically, a main vessel guidewire 62 is inserted into a main vessel 82 of the vessel bifurcation 80 to a point distal of the vessel bifurcation. A branch vessel guidewire 60 is advanced to the vessel bifurcation and inserted through an ostium or opening 86 of a branch vessel 84. A proximal end of the main vessel guidewire 62 is then inserted into the main guidewire lumen, and a proximal end of the branch vessel guidewire 60 is inserted into a branch guidewire lumen defined by the side catheter branch 14. See FIG. 4.

The catheter assembly 10 is advanced over the guidewires 60, 62 to the vessel bifurcation 80. See FIG. 5. The catheter assembly 10 is then advanced further distally until a distal end portion 56 of the side catheter branch 14 is positioned within the branch vessel 60. A marker system (described further below) can be used to help confirm proper radial and axial alignment of the lateral branch opening 54 of the sheath 52 relative to the ostium 86 into the branch vessel 84.

As the side catheter branch 14 follows the branch vessel guidewire 60, the side catheter branch 14 rotates about the main catheter branch 12 at the ring assembly 53. As the side catheter branch 14 rotates about the main catheter branch 12, the sheath 52, which is coupled to the side catheter branch 14, also rotates about the main catheter branch 12 so that the aperture 92 formed in the sheath 54 (see FIG. 2), is aligned with the ostium 86 of the branch vessel 84.

After proper positioning of the catheter assembly 10 is confirmed, the main and branch balloons 24, 26 are inflated. As the side balloon 26 is inflated, the inflatable portion 45 positioned at the aperture 92 extends through the aperture of the sheath 54. The remaining portions of the side balloon 26 contact and are held within the sheath 52 so that only the inflatable portion 45 extends through the aperture 92. The inflatable portion 45 contacts and moves the second cutting portions 68 of the cutting members 62, 64. As the inflatable portion 45 is further inflated, the second cutting portions 68 pivot in the directions 94, 96 with respect to the first cutting portions 66 so that the second cutting portions 68 engage the ostium 86 and/or the wall of the branch vessel 84. In this position, the first and second cutting portions 66, 68 of the cutting members 62, 64 can be used to cut any stenosis on the walls of the main or branch vessels 82, 84.

In one example, the sheath 52 can be moved axially within the main vessel 82 when the cutting members 62, 64 are in place to cause the cutting members 62, 64 to cut the stenosis in the vessels 82, 84 as desired. For example, in one arrangement, the second portion 57 of the ring assembly 53 can be released from the first component 55 once the catheter assembly 10 is in place so that the side catheter branch 14 can be moved axially with respect to the main catheter branch 12 to move the sheath 52 axially within the main vessel 82. In other arrangements, other therapies such as RF or electrical can be delivered to initiate cutting.

In some examples, additional therapy can be delivered after the cutting members 62, 64 are used to cut the stenosis. For example, in one arrangement, one or more drugs are delivered to further minimize restenosis after the walls of the vessels 82, 84 have been cut.

In another example, a bifurcated stent is delivered to the bifurcation 80 after the walls of the vessels 82, 84 are cut. For example, a stent (not shown) can be positioned about the sheath 54. After the cutting members 62, 64 are used to cut the stenosis, the sheath 54 can be removed from the catheter assembly 10, and the stent can then be delivered to the bifurcated vessel by further expansion of the main and side balloons 24, 26.

Other configurations are possible. For instance, in another example, the cutting members can be coupled directly to the stent. The cutting members can be made of a bioabsorbable material, such as iron or magnesium, so that, after delivery and cutting, the cutting members dissolve or otherwise dissipate over time.

It can be advantageous to use the cutting members 62, 64 to cut and create stress points on the walls of the main and/or side vessels 82, 84 adjacent to the ostium 86 because cutting of the area of the stenosis can minimize future restenosis of the area. For example, typically, the healthy portions of the blood vessel are more elastic than the heavily calcified regions of the stenosis. During deployment of therapy using balloons, the health portions of the blood vessel are therefore stretched more easily, which can cause stress-induced inflammatory effects leading to new stenoses. The use of the cutting members to cut the calcification associated with the stenoses allows the stenosis to be more easily expanded as well, thereby causing less stretching of the healthy blood vessel walls and the associated stress-induced inflammatory effects.

III. The Example Illustrated in FIG. 7

Referring now to FIG. 7, another example distal end portion 110 of a catheter assembly is shown. The distal end portion 110 is similar to that of the catheter assembly 10 described above, except that cutting members 162, 164 are coupled to the side balloon 26, rather than a sheath. The first cutting portion 66 of each cutting member 162, 164 is coupled to the balloon 26, and the second cutting portion 68 of each cutting member 162, 164 is coupled to the first cutting portion 66 so that the second cutting portion 68 can pivot with respect to the first cutting portion 66.

As the side balloon 26 is inflated as shown in FIG. 7, the inflatable portion 45 of the side balloon 26 contacts and moves the second cutting portion 68 of each of the cutting members 162, 164 so that the second cutting portions 68 pivot in directions 194, 196. In this manner, the first cutting portions 66 can be used to cut the wall of the main vessel, and the second cutting portions 68 can be used to cut the wall of the branch vessel of the bifurcation.

IV. The Example Illustrated in FIGS. 8 and 9

Referring now to FIG. 8, another example distal end portion 210 of a catheter assembly is shown. The distal end portion 210 includes a balloon 224 with a bulge 226 when inflated as shown in FIG. 8. Cutting members 262, 264 are coupled to the balloon 224. The first cutting portion 66 of each cutting member 262, 264 is coupled to the balloon 224, and the second cutting portion 68 of each cutting member 262, 264 is coupled to the first cutting portion 66 so that the second cutting portion 68 can pivot with respect to the first cutting portion 66.

As the balloon 224 is inflated as shown in FIG. 8, the bulge 226 contacts and moves the second cutting portion 68 of each of the cutting members 262, 264 so that the second cutting portions 68 pivots. In this manner, the first cutting portions 266 can be used to cut the wall of the main vessel, and the second cutting portions 268 can be used to cut the wall of the branch vessel at the bifurcation.

Referring now to FIG. 9, the balloon 224 is shown in a semi-folded state. A plurality of folds 228 are formed as the balloon 224 is folded to reduce the profile of the balloon 224 in the non-deployed state. An example of a balloon folded in such a manner is shown in U.S. Pat. No. 7,160,317 filed on Jan. 4, 2002, the entirety of which is hereby incorporated by reference. The cutting members 262 and 264 (not shown in this view) are positioned in the interior between two folds 228 of the balloon 224 so that the cutting members 262, 264 are shielded by the folds 228 of the balloon 224 until the balloon 224 is expanded. Upon expansion of the balloon 224, the folds 228 dissipate and the cutting members 262, 264 are exposed and moved to the cutting position shown in FIG. 8.

V. Alternative Arrangements for the Cutting Members

Referring now to FIG. 10, another arrangement for a distal end portion 310 of a catheter assembly is shown. The distal end portion 310 includes a plurality of cutting members 362, 363, 364, 365 coupled to the balloon 224. In the example shown, the cutting members 362, 364 are coupled to the balloon 224, and the cutting members 363, 365 are coupled to the bulge 226. The cutting members 362, 363, 364, 365 each form a "sharks tooth" or pyramid configuration with a pointed cutting surface 370. In this manner, the cutting members 362, 364 can be used to cut the wall of the main vessel, and the cutting member 363, 365 can be used to cut the wall of the branch vessel of the bifurcation. In the example shown, the cutting members 363, 364, 365, 366 are configured to fold laterally against the surface of the balloon 224 until the balloon 224 is inflated. For example, elastic members (not shown) made of a compliant material such as silicon rubber can be used to hold the cutting members 363, 364, 365, 366 against the surface of the balloon 224 prior to deployment.

Referring now to FIGS. 11-13, another example cutting member 462 is shown, which is similar to the cutting members 62, 64 shown in FIGS. 1-9. The cutting member 462 includes first and second cutting portions 466, 468. The second cutting portion 468 pivots about a point 472 in a direction 480 with respect to the first cutting portion 466. In example embodiments, the cutting member 462 is configured to allow the second cutting portion 468 to pivot to a specified angle a with respect to the first cutting portion 466. In some examples, the angle a is greater than 90 degrees. In other examples, the angle a is less than 90 degrees. In the examples in which the angle a is less than 90 degrees, the first and second cutting portions 466, 468 can create a "scissor-type" action that captures and cuts the vessel at the ostium between the first and second cutting portions 466, 468 to thereby enhance the cutting action of the cutting member 462. In example arrangements, the appropriate angle a is determined by the caregiver during a prescan of the bifurcation.

Other arrangements for the cutting members are possible. For example, in one alternative, each cutting member is broken into more than two portions that can pivot with respect to one another. In yet another example, each cutting member is made of a single portion. In yet another arrangement, some of the cutting members can be located on a sheath, and other cutting members can be located on the main or side balloons. Other configurations are possible.

The cutting members can be deployed at various points along the sheath and/or balloon to cut various portions of the walls of the main or branch vessels. In one alternative example, a plurality of cutting members are formed along the main balloon, side balloon, sheath, and/or an outer circumference of the side branch lumen to cut the walls of the main and/or side branch vessels at a plurality of sites. The cutting members can extend at one or a plurality of directions and/or orientations with respect to the other cutting members and the walls of the main and/or side branch vessels.

In yet another alternative, a kissing balloon arrangement can be used, in which a main balloon is positioned in the main vessel, and a side balloon is positioned along the main balloon. A distal part of the side balloon is positioned through the ostium into a branch vessel. Cutting members can be positioned along the side balloon, such as on the distal part that extends into the branch vessel. Upon inflation of the side balloon, the cutting members cut the vessel wall of the branch vessel, as described above. Other configurations are possible.

VI. Other Alternative Materials and Arrangements

In some arrangements, the distal end portions 30, 110, 210, 310 of the catheter assemblies can include marker material that is visible under X-ray or in fluoroscopy procedures. In some examples, the mark material is positioned along the distal end portions of the main and side catheter branches. Features of the system 10 that include marker material can be more easily identified and distinguished under X-ray or in fluoroscopy procedures. Some example marker materials include gold, platinum and tungsten. In one embodiment, the marker material can be included in a band structure that is secured to at least one of the main and side catheter branches 12, 14. In other embodiments, the marker material is part of the material composition of portions of the main and side catheter branches 12, 14. Viewability of features of the catheter assembly 10 under X-ray or fluoroscopy can assist the physician operating the system 10 to more easily adjust a position of the system 10 relative to the vessel bifurcation 80. Example markers and marker materials suitable for use with system 10 are described in U.S. Pat. No. 6,692,483 to Vardi, et al., and U.S. Provisional Patent Application Ser. No. 60/776,149, filed on Feb. 22, 2006, and titled MARKER ARRANGEMENT FOR BIFURCATION CATHETER, which patent matters are incorporated herein by reference.

Alternative catheter assemblies to those described above are configured for use with stents having self-expanding features. Self-expanding stents and self-expanding features of a stent typically do not require the use of an inflatable member such as a balloon to expand the sent or stent feature. Typically, self-expanding stents, such as those stents described in U.S. Published Patent Application No. 2004/0176837, are held in a constricted state using a sheath that fits over the stent. In the constricted state, the stent is able to navigate through a body lumen to the treatment site. Once the stent and sheath are positioned at the treatment side, the sheath is retracted proximally to release the stent for expansion of the stent into a radially expanded state.

A wide variety of stents, catheters, and guidewire configurations can be used with the catheter assembly embodiments of the present disclosure. The inventive principles disclosed herein should not be limited to any particular design or configuration. Some example stents that can be used with the catheter assemblies disclosed herein can be found in, for example, U.S. Pat. Nos. 6,210,429, 6,325,826 and 6,706,062 to Vardi et al., U.S. patent application Ser. No. 10/644,550, filed on Aug. 21, 2003, and titled STENT WITH A PROTRUDING BRANCH PORTION FOR BIFURCATED VESSELS, and U.S. Published Patent Application No. 2004/0176837 titled SELF-EXPANDING STENT AND CATHETER ASSEMBLY AND METHOD FOR TREATING BIFURCATIONS, the entire contents of which are incorporated herein by reference. In general, the aforementioned stents include a lateral branch opening located between distal and proximal open ends of the stent. The lateral branch opening defines a path between an inner lumen of the stent and an area outside of the stent. The stent lateral branch opening is distinct from the cell openings defined between strut structures from which the stent sidewall is constructed. In some stents, the lateral branch opening can be surrounded by expandable structure. The expandable structure can be configured to extend radially into the branch lumen of the bifurcation upon expansion of, for example, an inflatable portion of the bifurcation treatment system. Typically, the stent is expanded after being positioned in the main lumen with the lateral branch opening aligned with an opening into the branch lumen. Alignment of the lateral branch opening with the opening into the branch lumen includes both radial and axial alignment. The stent, including the expandable structure surrounding the lateral branch opening, can be expanded with a single expansion or multiple expansions using one or more inflatable members.

The main and side balloons, and all other balloons disclosed herein, can be made of any suitable balloon material including compliant and non-compliant materials and combinations thereof. Some example materials for the balloons and catheters disclosed herein include thermoplastic polymers, polyethylene (high density, low density, intermediate density, linear low density), various co-polymers and blends of polyethylene, ionomers, polyesters, polycarbonates, polyamides, poly-vinyl chloride, acrylonitrile-butadiene-styrene copolymers, polyether-polyester copolymers, and polyetherpolyamide copolymers. One suitable material is SURLYN®, a copolymer polyolefin material (DuPont de Nemours, Wilmington, Del.). Still further suitable materials include thermoplastic polymers and thermoset polymeric materials, poly(ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid L2101 1F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356, which is incorporated herein by reference.

VII. Conclusion

As described herein, example arrangements include a catheter assembly catheter assembly for deployment in a bifurcated vessel. The catheter assembly includes a catheter shaft extending from a proximal end portion to a distal end portion, and a balloon operatively coupled to the distal end portion of the catheter shaft. The catheter assembly also includes a sheath positioned about the balloon, the sheath including at least one cutting member coupled thereto. As the balloon is inflated, the cutting member is moved to a position to cut a portion of a main vessel and/or the bifurcated vessel. In some examples, the cutting member includes first and second portions, the first portion being coupled to and pivoting with respect to the second portion to cut the bifurcated vessel. In this manner, restenosis of the bifurcated vessel is minimized.

It is noted that not all of the features characterized herein need to be incorporated within a given arrangement, for the arrangement to include improvements according to the present disclosure.

What is claimed is:

1. A catheter assembly for deployment in a vessel, the assembly comprising:
   a catheter shaft extending from a proximal end portion to a distal end portion;
   a balloon operatively coupled to the distal end portion of the catheter shaft;
   a sheath positioned about the balloon, the sheath including at least one cutting member coupled thereto, wherein, as the balloon is inflated, the cutting member is moved to a position to cut a portion of the vessel;
   wherein the cutting member defines a first cutting portion and a second cutting portion, the second cutting portion being configured to pivot relative to the first cutting portion to cut a wall of a bifurcated vessel;
   wherein the first cutting portion is coupled to the sheath, and the second cutting portion is coupled to the first cutting portion; and
   wherein the sheath defines an aperture, and wherein the second cutting portion is positioned to extend over the aperture such that, as the balloon is inflated, the balloon is configured to extend through the aperture and pivot the second cutting portion relative to the first cutting portion.

2. A method for forming a catheter assembly for deployment in a bifurcated vessel, the method comprising:
   providing a catheter shaft extending from a proximal end portion to a distal end portion;
   coupling a balloon to the distal end portion of the catheter shaft;
   surrounding the balloon with a tubular sheath;
   defining an aperture in the tubular sheath through which the balloon extends upon inflation;
   positioning a cutting member relative to the balloon, wherein the cutting member is coupled to an outer surface of the tubular sheath; and inflating the balloon to move the cutting member towards a wall of a blood vessel to cut the wall;

wherein positioning the cutting member further comprises positioning a cutting portion of the cutting member to extend over the aperture so that the balloon contacts and rotates the cutting portion upon inflation.

3. The method of claim 2, wherein inflating the balloon further comprises (i) allowing the balloon to pivot a second cutting portion of the cutting member relative to a first cutting portion of the cutting member.

4. The method of claim 2, wherein coupling the balloon further comprises (i) coupling a main balloon and a side balloon to the distal end portion of the catheter shaft, wherein the side balloon moves the cutting member to the position to cut the wall.

\* \* \* \* \*

UNITED STATES PATENT AND TRADEMARK OFFICE
CERTIFICATE OF CORRECTION

| | | |
|---|---|---|
| PATENT NO. | : 7,842,056 B2 | Page 1 of 1 |
| APPLICATION NO. | : 11/750748 | |
| DATED | : November 30, 2010 | |
| INVENTOR(S) | : Thomas J. Holman and Jan Weber | |

It is certified that error appears in the above-identified patent and that said Letters Patent is hereby corrected as shown below:

Column 7
Line 57: delete "angle a" and insert therefor -- angle $\alpha$ --.
Line 59: delete "angle a" and insert therefor -- angle $\alpha$ --.
Line 60: delete "angle a" and insert therefor -- angle $\alpha$ --.
Line 61: delete "angle a" and insert therefor -- angle $\alpha$ --.
Line 66: delete "angle a" and insert therefor -- angle $\alpha$ --.

Signed and Sealed this
First Day of February, 2011

David J. Kappos
*Director of the United States Patent and Trademark Office*